United States Patent [19]

Gaucher

[11] Patent Number: 4,478,731

[45] Date of Patent: Oct. 23, 1984

[54] AQUEOUS LUBRICATING COMPOSITION AND PROCESS OF MANUFACTURING SAME

[75] Inventor: Antoine Gaucher, Saint Etienne, France

[73] Assignee: Centre Stephanois De Recherches Mecaniques Hydromecanique Et Frottement Zone Industrielle, Boutheon-Loire, France

[21] Appl. No.: 516,182

[22] Filed: Jul. 21, 1983

Related U.S. Application Data

[63] Continuation of Ser. No. 073,803, Sep. 10, 1979, abandoned.

[30] Foreign Application Priority Data

Sep. 8, 1978 [FR] France ................................ 78 26376

[51] Int. Cl.$^3$ ............................................. C10M 3/18
[52] U.S. Cl. ........................................ 252/36; 252/35; 252/49.3
[58] Field of Search ........................... 252/35, 36, 49.3

[56] References Cited

U.S. PATENT DOCUMENTS

| | | | |
|---|---|---|---|
| 1,767,076 | 6/1930 | Jarman | 252/35 |
| 2,628,895 | 2/1953 | Murray et al. | 252/35 X |
| 3,055,829 | 9/1962 | Wiley et al. | 252/35 X |
| 3,262,889 | 7/1966 | Edwards et al. | 252/35 X |
| 3,313,729 | 4/1967 | Glasson | 252/49.3 X |
| 3,519,571 | 7/1970 | Szczepanek et al. | 252/36 X |
| 4,029,682 | 6/1977 | Foulks, Jr. | 252/35 X |

FOREIGN PATENT DOCUMENTS

| | | | |
|---|---|---|---|
| 559860 | 3/1944 | United Kingdom | 252/36 |
| 833868 | 5/1960 | United Kingdom | 252/49.3 |

OTHER PUBLICATIONS

Bastian, "Metalworking Lubricants", 1951, p. 19.

*Primary Examiner*—Andrew Metz
*Attorney, Agent, or Firm*—Gifford, VanOphem & Sprinkle

[57] ABSTRACT

A process for the production of an aqueous lubricant composition free of oil including water and at least one metallic carboxylate, wherein the anionic is at least one saturated linear organic radical containing at least 12 carbon atoms and the cationic is at least one bivalent or trivalent metal having an electro-chemical oxidation-reduction potential greater than −0.7 volts. The process includes mixing of two mother solutions. The first mother solution is an aqueous solution of at least one alkali metal carboxylate soluble in water wherein the anionic is at least one saturated linear organic radical with at least 12 carbon atoms. The second mother solution is an aqueous solution of at least one metallic salt whereof the anionic is selected from the group consisting of hydroxide, chloride, sulphate, nitrate or phosphate ions and whereof the cationic is at least one bivalent or trivalent metal having an electro-chemical oxidation reduction potential greater than −0.70 volts.

20 Claims, 4 Drawing Figures

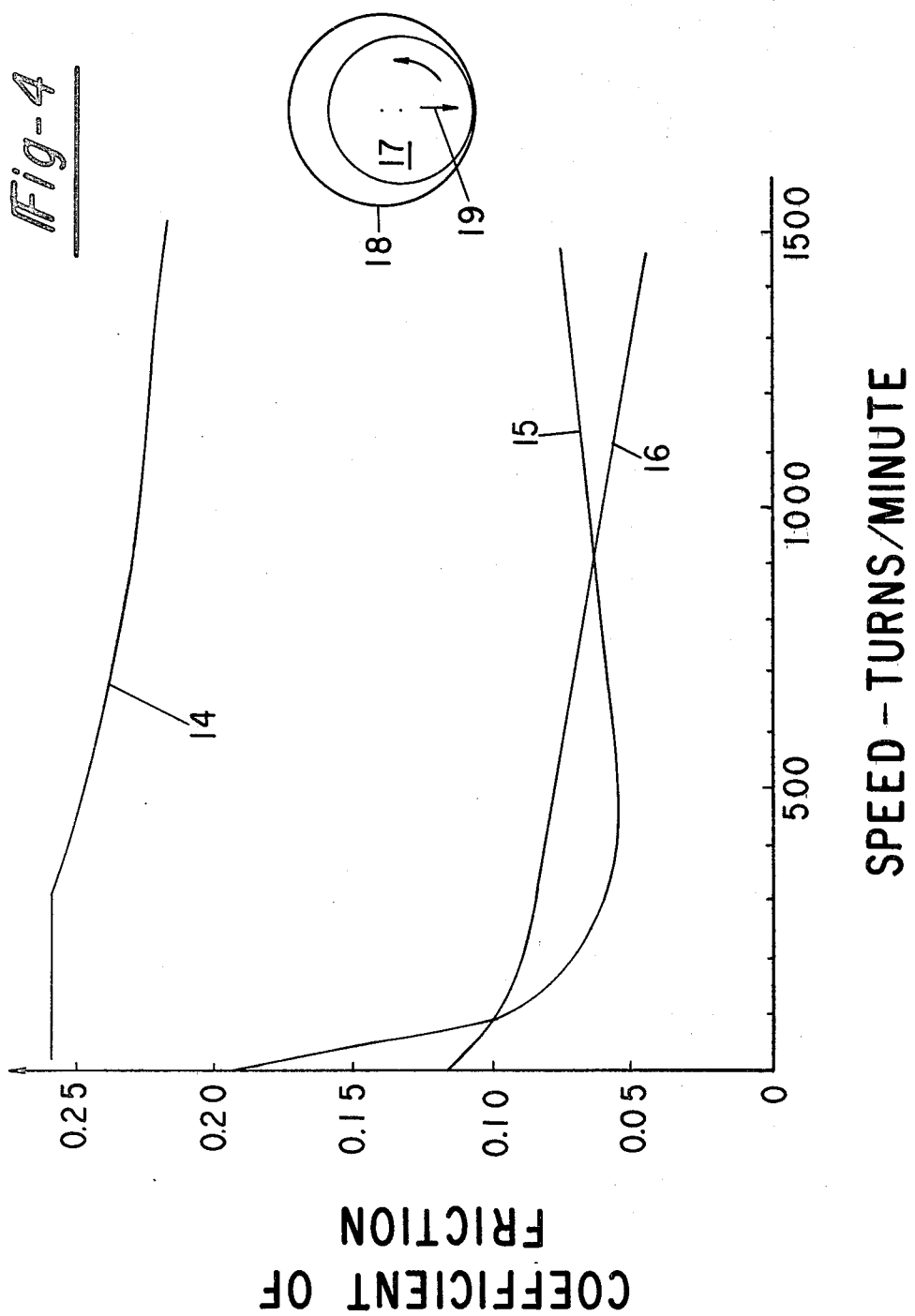

AQUEOUS LUBRICATING COMPOSITION AND PROCESS OF MANUFACTURING SAME

This is a continuation, of application Ser. No. 073,803, filed Sept. 10, 1979 now abandoned.

BACKGROUND OF THE INVENTION

1. Field of the Invention

The present invention relates to a novel aqueous lubricating composition and the process of manufacturing same.

2. Description of the Prior Art

A water-based lubricant is of particular interest to the engineering industry which has need of an economical fluid which does not employ a traditional hydrocarbon-based lubricant and which performs better than the existing water-based lubricants. Examples of these are a non-flammable fluid for use in mines, a fluid for improving the reliability of metal-forming operations and increasing the rate of such operations, a fluid with a high degree of heat conduction in the order to make new mechanical concepts possible, and economical fluid for the lubricating tools in boring and other operations.

Numerous compositions have already been proposed for such purposes, as for example soap solutions and oil-water emulsions possibly mixed with a fatty acid.

The present invention relates more particularly to lubrication employing metallic salts of fatty acids or metallic carboxylates. Alkali metals or alkaline earth metal stearates have been investigated previously.

Two principal difficulties and limitations have been encountered in using these products, namely (1) The lubricating power of these products is relatively mediocre and is incompatible with severe industrial uses. It is necessary to use in addition to the aforesaid metallic soaps, additives for use under extreme pressure (2) The majority of metallic carboxylates are substantially insoluble in water. The only exception to this rule are certain alkali metal carboxylates, notably those of sodium, but their lubricating power is, however, mediocre. It is thus necessary to use metallic carboxylates suspended in water. This requires the use of dispersing agents. Moreover, it is well known that the suspensions obtained are relatively unstable and that they precipitate in from several minutes to several hours. It thus becomes necessary to use stabilizing agents.

It has been proposed to use compositions including one or more alkali metal carboxylates; one or more surface active agents and a dispersing agent; certain organic compositions as stabilizing agents; and certain sulphur or chlorine agents as extreme pressure agents for example, French Patent Specification No. 2158265 (Parker) discloses an aqueous suspension of stearates of calcium, magnesium, aluminum and barium, as dispersents anionic, cationic non-ionic surface active agents, a composition acting as a stabilizer, and chlorinated paraffin, and/or sulphonated fatty oil as extreme pressure additives.

In the prior art there is no aqueous-based lubricant strictly free of oil which is both stable and effective

SUMMARY OF THE INVENTION

The present invention provides such a lubricant.

According to the present invention there is provided a process for the production of an aqueous lubricant composition free of oil including water and at least one metallic carboxylate, wherein the anionic part of the carboxylate is at least one saturated linear organic radical containing at least 12 carbon atoms and the cationic part being formed of at least one bivalent or trivalent metal having an electro-chemical oxidation-reduction potential greater than $-0.7$ volts, wherein the process includes mixing two mother solutions, the first mother solution consisting of an aqueous solution of at least one alkali metal carboxylate soluble in water whereof the anionic part is at least one saturated linear organic radical with at least 12 carbon atoms and the second mother solution is an aqueous solution of at least one metallic salt whereof the anionic part is selected from the group consisting of hydroxide, chloride, sulphate, nitrate or phosphate ions and whereof the cationic part is at least one bivalent or trivalent metal having an electro-chemical oxidation-reduction potential greater than $-0.70$ volts.

The alkali metal carboxylate is preferably sodium carboxylate which, in the first mother solution, is used in an amount of greater than 7 grams/liter. It is preferred that the amount of sodium present in the first mother solution is in excess with respect to the amount required to convert all of the metal in the second solution to the metal carboxylate.

Preferably also the saturated linear organic radical of the carboxylate contains 18 to 22 carbon atoms.

Preferably also the metal having an electro-chemical oxidation-reduction potential above $-0.7$ volts is selected from cadmium, cobalt, copper, indium, nickel, lead, tin and zinc.

It is preferred that, once the two mother solutions have been mixed, the resultant solution is heated to a temperature of 40° to 70° C.

If desired, there may also be included additives such as, for example, corrosion inhibitors, detergent agents or anti-frothing agents, or other products.

BRIEF DESCRIPTION OF THE DRAWINGS

The invention will be further explained, by way of example, with reference to the accompanying drawings, in which:

FIGS. 3 and 4 are diagrams showing the evolution of the coefficient of friction as a function of the speed of rotation in the case of different compositions.

DETAILED DESCRIPTION OF THE PREFERRED EMBODIMENT

Figure 1:
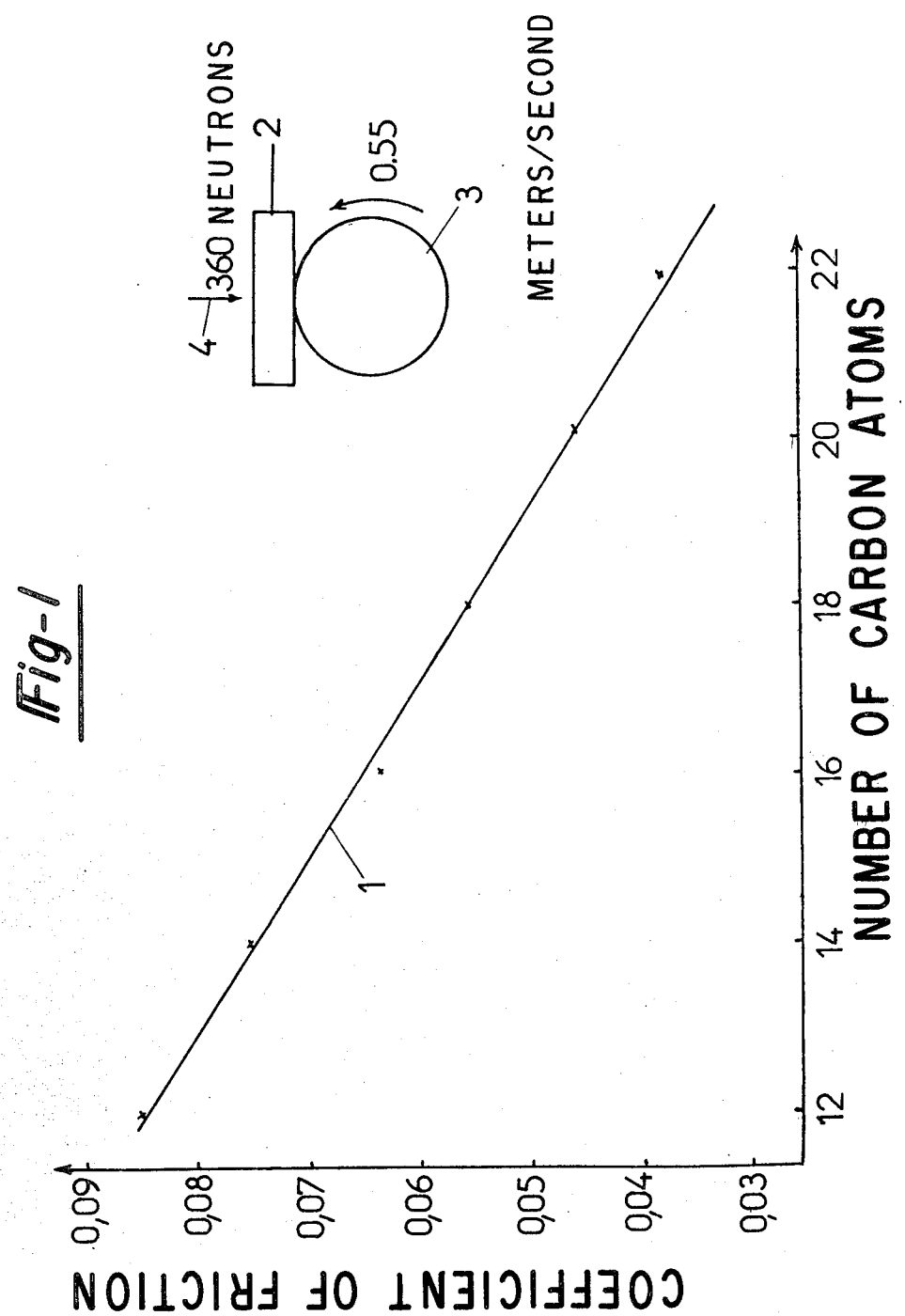
FIG. 1 is a diagram showing the influence of the length of the cationic carboxylate chain relative to the coefficient of friction.

The role played by the anionic fatty chain in a lubricant has been shown by experiments carried out by the Applicant. These experiments are illustrated by the curve 1 of FIG. 1, this curve representing the evolution, as a function of the number of carbon atoms in the chain, of the coefficient of friction obtained by rubbing on the plain face of a parallelepipeded plate 2 a rotatable cylindrical bearing 3 with the application of a force 4. For a number of carbon atoms between 12 and 22 all the values of coefficient of friction are below 0.1. In particular, it is to be noted, that very low values are attained with carbon atoms above 16. These values are remarkably lower than those obtained, all other things being equal, with a conventional oil incorporating zinc dithiophosphate.

Figure 2:
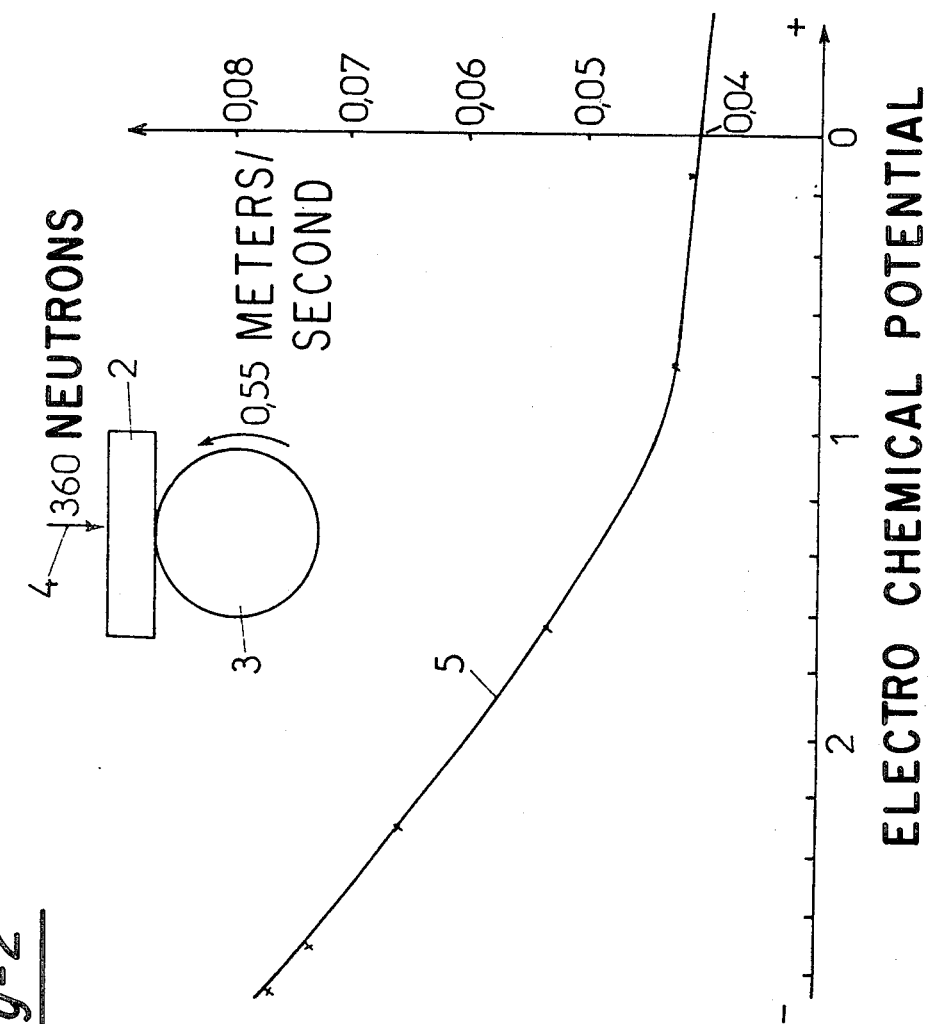
FIG. 2 is a diagram showing the influence of the kind of metal and its electro-chemical oxidation reduction potential on the coefficient of friction.

These experiments show the role played by the cationic part of fatty acid salt, which have resulted in the discovery of the existence of a threshold of electrochemical reduction potential below which a lubricating power of the suspension obtained remains mediocre while beyond this threshold it becomes excellent. This threshold is in the region of −0.70 volts. This is illustrated in FIG. 2 wherein the curve 5 represents the evolution as a function of the oxidation-reduction potential of the metal, of the coefficient of friction obtained under the same conditions as referred to in FIG. 1. This is accomplished by rubbing a rotatable cylindrical bearing 3 against a plate 2 under the action of a force 4. As shown previously, the superficial speed of the bearing or roller 3 may be of the order of 0.55 meters per second while the force 4 may be of the order of 360 Newtons. It should be noted in particular that better results are obtained for metals whose oxidation-reduction potential is greater than −0.70 volts than the results obtained with oils incorporating zinc dithiophosphate.

The Applicant has also studied very precisely the stability of the suspensions obtained. This study has resulted in the discovery, quite unexpectedly, that it is perfectly possible to create a stable suspension without making use of conventional surface active agents and/or stabilizing agents. The discovery lies in the fact that a perfect stability of the suspension is obtained when the metallic carboxylate is not directly mixed with the water but produced "in situ" by mixing two mother solutions, the first being an aqueous solution of one of the alkali metal carboxylates soluble in water and the second being an aqueous solution of a metallic salt whereof the anionic part is selected from the group of hydroxide, chloride, sulphate, nitrate and phosphate ions and whereof the cationic part is a bivalent or trivalent metal. To facilitate the formation "in situ" of the metallic carboxylate, it is advantageous after having mixed the two mother solutions, to heat the resulting solution to a temperature not exceeding 70° C. It is equally advantageous if the quantity of the first mother solution is such that the quantity of carboxylate which it contains is slightly in excess of that which is necessary to produce the following exchange reaction of a kind where the mother solution carrying the bivalent metal or trivalent metal is a chloride solution.

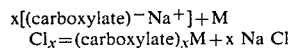

$$x[(\text{carboxylate})^-\text{Na}^+] + M Cl_x = (\text{carboxylate})_x M + x\, Na\, Cl$$

wherein M is the bivalent or trivalent metal and x is equal to 2 or 3.

In sum the composition according to the invention is a suspension of metallic salts of fatty acids (or metallic carboxylates). This composition is characterized as follows:

The anionic part of the metallic salt is a saturated linear organic radical containing more than 12 carbon atoms and preferably from 18 to 22 carbon atoms.

The cationic part is a bivalent or trivalent metal whose electro-chemical oxidation-reduction potential is greater than −0.70 volts.

The metallic carboxylate is formed "in situ" by mixing two mother solutions, namely a first aqueous solution of an alkali metal carboxylate, preferably a sodium carboxylate, a second aqueous solution of a metallic salt wherein the anionic is selected from the group consisting of hydroxide, chloride, sulphate, nitrate, phosphate and wherein the cationic is a bivalent or trivalent metal whose oxidation-reduction potential is greater than −0.70 volts.

The composition as defined has numerous advantages. Besides being strictly free of oil it is perfectly stable and is highly efficient as will be seen from the two Examples set out hereinafter.

It is to be understood that the composition according to the invention is not limited to a single mixture of water and metallic salt of a fatty acid but it can include either several of these salts or other substances such as corrosion inhibitors, detergent agents, anti-frothing agents, and others.

EXAMPLE 1

Figure 3:
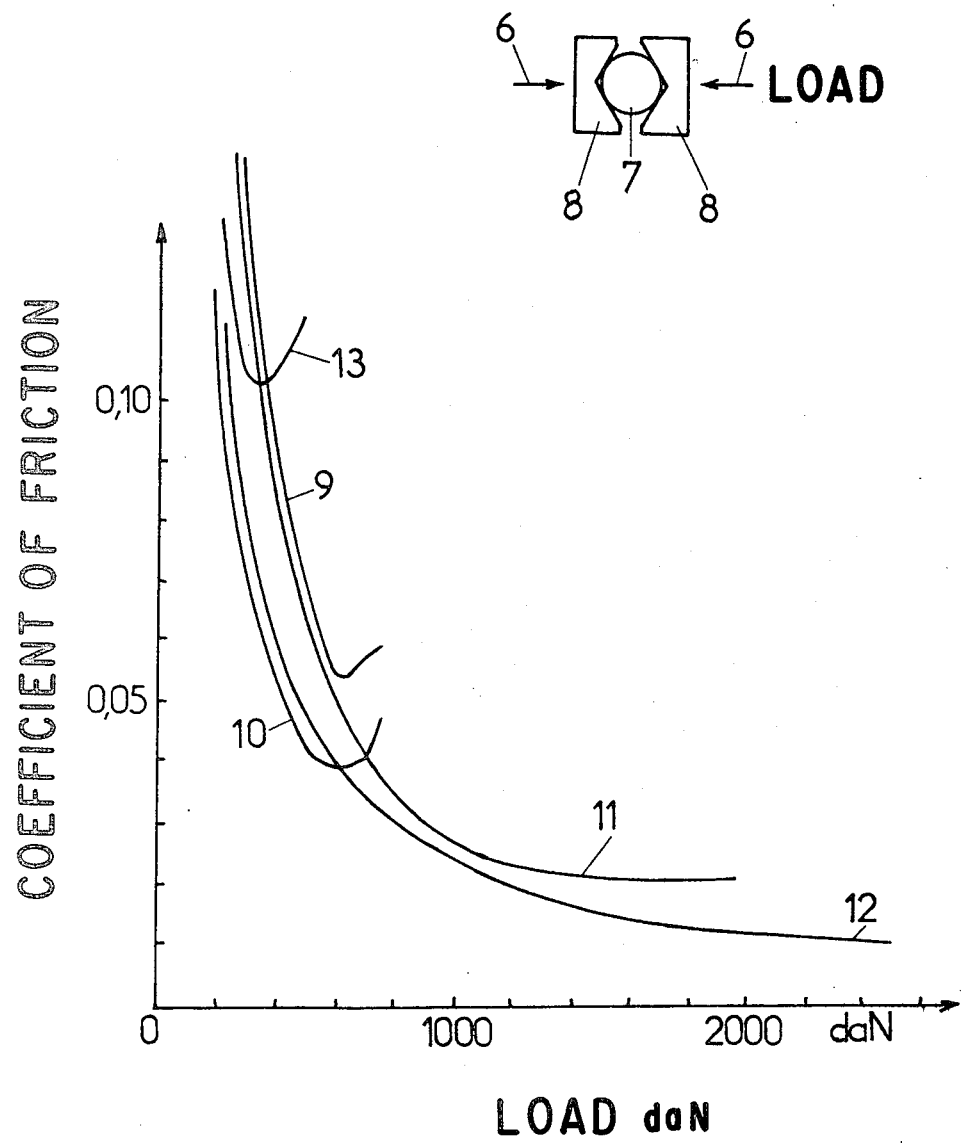

The experiment was conducted by increasing in continuous fashion the clamping load 6 on a cylindrical test bar 7 rubbing between two V jaws 8 (FIG. 3), the test bar being annealed is a steel XC 35. By repeating the operation in the presence of different lubricants it can be seen that the binding or ceasing load depends on the nature of the lubricant. Curves 9 to 13 each represent variations in the coefficient of friction as a function of the clamping load 6 in the presence of a different lubricant.

In the case of curve 9 the lubricant is an oil based lubricant incorporating zinc dithiophosphate. Ceasing occurs with a clamping load equal to about 650 daN.

In the case of curve 10 the lubricant is lead behenate and it acts as a dry lubrication. Ceasing occurs for a clamping load of about 600 daN.

In the case of curve 11 the lubricant is an oil based lubricant incorporating lead dithiophosphate and lead behenate, the ceasing occurring for a clamping load of about 1800 daN.

In the case of curve 12 there is used a lubricant according to the invention with lead behenate. Ceasing does not occur for a clamping load greater than 2500 daN. In this example the lubricating composition according to the invention has been prepared from sodium behenate wherein, conforming to the invention, the anionic part is a saturated linear organic radical 22 carbon atoms and with the cationic is lead. Lead is a bivalent metal whose the electrochemical oxidation reduction potential is equal to −0.13 volts, that is to say greater than −0.70 volts. Similarly the lubricating composition has been prepared according to the invention by mixing two mother solutions with the first being an aqueous solution of sodium behenate while the second is an aqueous solution of lead chloride.

In the case of curve 13 the lubricant is water.

EXAMPLE 2

This example illustrates the influence of the method of preparation of the lubricating solutions on stability of the solutions.

A solution containing 1 liter of water, 10 grams of zinc stearate and 1 gram of anionic surface active agent has developed a height or depth of precipitant equal to 12 millimeters contained in a glass tube of 8 centimeters in diameter 24 hours after it had been formed.

A solution of zinc stearate, according to the invention, obtained by mixing equal parts of an aqueous solution of sodium stearate in an amount of 0.0458 mole/liter with an aqueous solution of zinc chloride in an amount of 0.00914 mole/liter, after heating the mixture over a period of 10 minutes to 60° C. presents no trace of precipitate after more than 3 months.

FIG. 4 shows that this solution according to the invention possesses remarkable lubricating properties. This diagram includes curves 14, 15 and 16 representing, in the presence of different lubricants, variations in a coefficient of friction as a function of the speed of movement of a steel shaft 17 rubbing in bearing 18 under a load of 19 to 213 Newtons.

In the case of the curve 14 the lubricant used is water. In case of the curve 15 the lubricant is composed of oil incorporating zinc dithiophosphate. Curve 16 is a lubricant according to the invention consisting of the solution of zinc stearate in the aforesaid aqueous medium.

I claim:

1. A process for the production of an aqueous lubricant composition comprising the steps of:
    creating a first mother solution comprising an aqueous solution of at least one alkali metal carboxylate which is water soluble, wherein the anionic moiety of said alkali metal carboxylate comprises a saturated linear organic radical having at least twelve carbon atoms;
    creating a second mother solution comprising an aqueous solution of at least one metallic salt, wherein the anionic moiety of said metallic salt is selected from the group consisting of hydroxide, chloride, sulphate, nitate and phosphate ions, and wherein the cationic moiety of said metallic salt is selected from the group consisting of bivalent and trivalent metal ions having an electro-chemical oxidation-reduction potential greater than about $-0.7$ volts;
    mixing said first and second mother solutions together to form a mixture thereof; and
    heating said mixture to a temperature of between about forty degrees centigrade and about seventy degrees centigrade;
    wherein the concentration and volume of said first solution are selected so as to provide a stoichiometric excess of carboxylate in said mixture, relative to the concentration of said at least one metallic salt in a given volume of said second solution;
    wherein said process is characterized by the absence of the addition of, and the selection of reactants free of, any other oil, surface active agents, and stabilizing agents; and
    wherein said at least one alkali metal carboxylate and said at least one metallic salt are selected so that the metallic carboxylate so formed does not precipitate from said mixture;
    whereby a stable aqueous lubricant composition comprising water and at least one metallic carboxylate, free of added oil, surface active agents, and stabilizing agents, is provided.

2. The process of claim 1 wherein said alkali carboxylate is a sodium carboxylate.

3. The process of claim 2 wherein the concentration of sodium carboxylate used in the preparation of said first mother solution is greater than seven grams per liter.

4. The process of claim 1 wherein said saturated linear organic radical contains eighteen to twenty-two carbon atoms.

5. The process of claim 1 wherein said cationic moiety of said metallic salt is selected from the group consisting of cadmium, cobalt, copper, indium, nickel, lead, tin, and zinc ions.

6. The method of claim 1 wherein said alkali carboxylate comprises sodium behenate, and said metallic salt comprises lead chloride, whereby said metal carboxylate comprises lead behenate.

7. The method of claim 1 wherein said alkali carboxylate comprises sodium stearate, and said metallic salt comprises zinc chloride, whereby said metal carboxylate comprises zinc stearate.

8. The method of claim 1 wherein said second mother solution comprises an aqueous solution of zinc chloride in an amount of 0.00914 moles per liter and wherein said first mother solution comprises an aqueous solution of sodium stearate in an amount of 0.0458 moles per liter.

9. The method of claim 8 wherein said mixing steps comprises mixing equal volumes of said first and second mother solutions.

10. The process of claim 9 wherein said heating step comprises heating said mixture at a temperature of sixty degrees centigrade for ten minutes.

11. The method of claim 1 further comprising the addition of at least one additive to one of said solutions, said at least one additive being selected from the class consisting of corrison inhibitors, detergent agents, and anti-frothing agents.

12. The process of claim 11 wherein said alkali carboxylate is a sodium carboxylate.

13. The process of claim 12 wherein the concentration of sodium carboxylate used in the preparation of said first mother solution is greater than seven grams per liter.

14. The process of claim 11 wherein said saturated linear organic radical contains eighteen to twenty-two carbon atoms.

15. The process of claim 1 wherein said cationic moiety of said metallic salt is selected from the group consisting of cadmium, cobalt, copper, indium, nickel, lead, tin, and zinc ions.

16. The stable aqueous lubricant composition obtained by the process of claim 1.

17. The stable aqueous lubricant composition obtained by the process of claim 6.

18. The stable aqueous lubricant composition obtained by the process of claim 7.

19. The aqueous lubricant composition obtained by the method of claim 10.

20. The stable aqueous lubricant composition obtained by the process of claim 11.

* * * * *

UNITED STATES PATENT AND TRADEMARK OFFICE
CERTIFICATE OF CORRECTION

PATENT NO. : 4,478,731
DATED : October 23, 1984
INVENTOR(S) : Antoine Gaucher

It is certified that error appears in the above-identified patent and that said Letters Patent is hereby corrected as shown below:

Column 1, line 33, after "namely" insert a colon ---- : ----.

Column 1, line 38, after "pressure" insert a period ---- . ----.

Column 1, line 63, after "effective" insert a period ---- . ----.

Column 2, line 66, delete the comma ",".

Column 3, line 54, delete "In sum the" and insert ---- The ----.

Column 4, line 44, after "radical" insert ---- with ----.

Column 4, line 45, delete "with".

Column 4, line 57, before "stability" insert ---- the ----.

Signed and Sealed this

Twenty-first Day of May 1985

[SEAL]

Attest:

DONALD J. QUIGG

Attesting Officer  Acting Commissioner of Patents and Trademarks